United States Patent
Sarhan et al.

(10) Patent No.: US 6,627,793 B2
(45) Date of Patent: *Sep. 30, 2003

(54) LOW TEMPERATURE-INDUCIBLE WHEAT WCS120 GENE PROMOTER

(75) Inventors: Fathey Sarhan, Saint Laurent (CA); Francois Ouellet, Montreal (CA)

(73) Assignee: Université du Québec A Montréal, Montréal (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/220,794

(22) Filed: Dec. 28, 1998

(65) Prior Publication Data

US 2003/0065162 A1 Apr. 3, 2003

(30) Foreign Application Priority Data

May 20, 1998 (CA) ............................................. 2238137

(51) Int. Cl.⁷ .................. C12N 15/82; C12N 15/90; C12N 5/04; C12N 15/87; A01H 5/00
(52) U.S. Cl. ................... 800/278; 435/69.1; 435/320.1; 435/468; 536/24.1; 800/289; 800/298; 800/306; 800/320
(58) Field of Search .............................. 435/69.1, 320.1, 435/468, 419, 410; 536/23.6, 24.1; 800/278, 288, 289, 295, 298, 320, 320.3

(56) References Cited

PUBLICATIONS

Ouellet et al, FEBS Lett., vol. 423, pp. 324–328, 1998.*
Kim et al, Plant Mol. Biol, vol. 24, pp. 105–117, 1994.*
White et al, Plant Physiol., vol. 106, pp. 917–928, 1994.*
Chauvin et al, Plant Physiol., vol. 105, pp. 1017–1018, 1994.*

Peng et al, Theor. Appl. Genet., vol. 83, pp. 855–863, 1992.*

Francois Ouellet et al., The wheat wcs 120 promoter is cold–inducible in both monocotyledonous and dicotyledonous species, FEBS Letters 423 (1998), pp. 324–328.*

Mario Houde et al., Cloning, Characterization, and Expression of a cDNA Encoding a 50–Kilodalton Protein Specifically Induced by Cold Acclimation in Wheat 1, Plant Physiol. (1992) 99, pp. 1381–1387.*

A. Vazquez–Tello et al., Low temperature–stimulated phosphorylation regulates the binding of nuclear factors to the promoter of Wcs 120, a cold–specific gene in wheat, Mol. Gen Genet (1998) 257: pp. 157–166.*

Genbank listing for entry AF031235, Vazquez–Tello et al. (1998) Triticum aestivum cold specific protein (wcs 120) gene, promoter sequence, 2 pages.

* cited by examiner

Primary Examiner—Ashwin Mehta
(74) Attorney, Agent, or Firm—Nixon & Vanderhye P.C.

(57) ABSTRACT

The Wcs120 gene encodes a highly abundant protein which appears to play an important role during cold acclimation of wheat. To understand the regulatory mechanism controlling its expression at low temperature (LT-responsiveness), the promoter region has been characterized. The data indicate the involvement of putative enhancer elements, negative and positive regulatory regions in the transcriptional regulation of this gene. Further, the promoter was found to be cold-inducible in different freezing tolerant and sensitive monocot and dicot species, suggesting that universal transcription factors responsive to LT may be present in all plants. Therefore this promoter could be used to drive the genes needed for LT tolerance in sensitive species.

22 Claims, 10 Drawing Sheets a

```
-860 AAACCACGGG TTTTTGGCCG GATCCGTGGC GGGGGACGAC
-820 AACGCGGTCA GTCGCGGCAG AGGCGGCGTC GGACATCGGG
-780 CCGTTCACGT CCGCGGTGTC GGACGGGGAC GGTGAGATGC
-740 GGTGTCGAAC GTCGGGCCGT TCACGTCCGC GTCGTCGGAC
-700 GGGCACGGTG AGATGCGGCG TCGGCGGGG TTGGGACGGC
-660 GGCGATCGGC CAGTTGGAAA AATGGAACGG GAGGAGCATG
-620 ATCGCCGGGC GGGCGAGAAG ATCATGCAAC TGCCTCTTTT
-580 TTCCCGTACA CGGGCGATGC CTTTTTTTTT GCATCCGCGC
-540 GGGTATACGT CGTCGGACCT GTATGTACAA TAGAAGGTGG
-500 GTATATCGTT TCCTTCATAT GGCCATTCTG CCCTTCTACA
-460 TTTTGTTGGG GGTCTACCGA AGCACTTCTC AGAATCCTAC
-420 TGTATAAAAT TATTTCGAAT CAAAGCCCTA AGCCTCTCGT
-380 ATGCTTCTTC TAGTTACTCT CATAGTCTCA TTGTCGTTAC
-340 ATGCCGACAC TTTGGATCTT CCATCCTCTT AAGCAAACAA
-300 TACTACCATT TTTGCAAGAG AAAAGAATCA TCTTCTTCCC
-260 GGACAAGGAC GAATGAGCTG GGACGTGGCG ACCCGGACGC
-220 GCCACTGGCT TCAGAGGCCC GGCCCCCCTA GTCGGCAGCC
-180 ACCTGCCGAC CACTGATGCG ACCACACGTA GCTCCCAGCC
-140 GCGGCGATTC GTCCATCTGA CCAGCCCTCT TTATGGGCTA
-100 GTCGGCACTC ACCTGCCCAT CCACTCACGA GCGCGCACGT
-60  CGTGGTTCGT ATACCCTCCA ACGGCCTATA AATACTGCGT
-20  CGCGCTGCAT ATGCTTTACA caaccacctg cttcacacta
+21  ccaaggcaag tacacagcag caatacgtag tagatttccc
+61  gagtgaggag ctcagcgcaa gatg
``` b

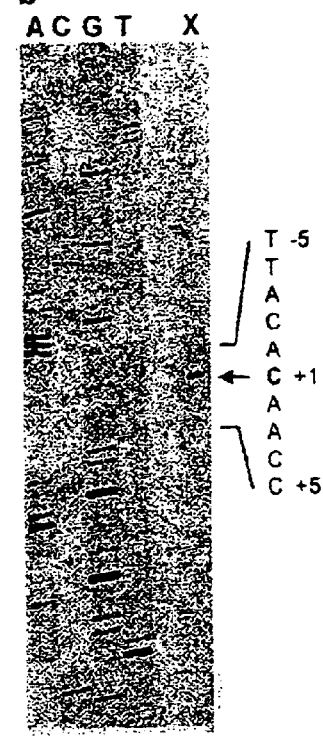

Figure 1

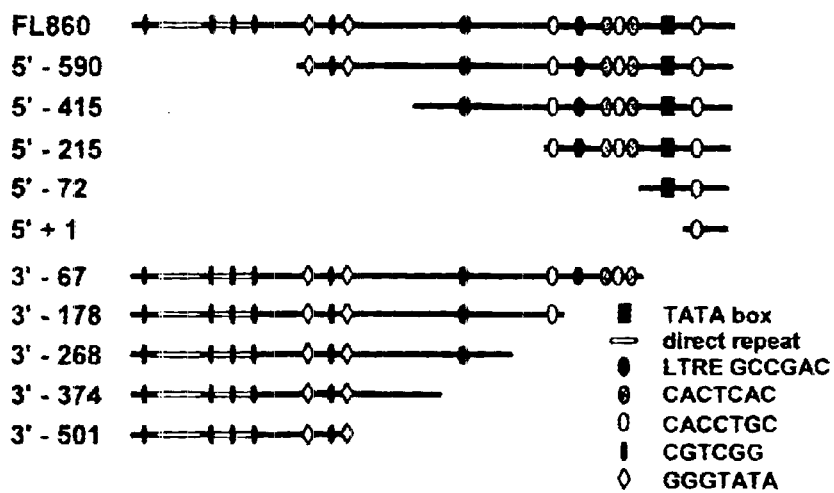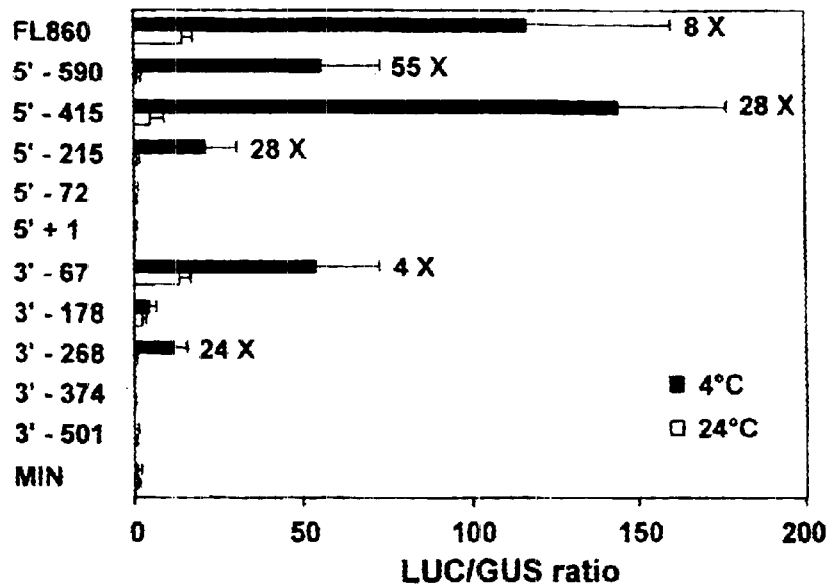
Figure 9

SEQUENCE LISTING

<160> NUMBER OF SEQ ID NOS: 23

<210> SEQ ID NO 1
<211> LENGTH: 944
<212> TYPE: DNA
<213> ORGANISM: Triticum aestivum

<400> SEQUENCE: 1

```
aaaccacggg ttttggccg gatccgtggc ggggacgac aacgcggtca gtcgcggcag     60
aggcggcgtc ggacatcggg ccgttcacgt ccgcggtgtc ggacggggac ggtgagatgc    120
ggtgtcgaac gtcgggccgt tcacgtccgc gtcgtcggac gggcacggtg agatgcggcg    180
tcgggcgggg ttgggacggc ggcgatcggc cagttggaaa aatggaacgg gaggagcatg    240
atcgccgggc gggcgagaag atcatgcaac tgcctctttt ttcccgtaca cgggcgatgc    300
ctttttttt gcatccgcgc gggtatacgt cgtcggacct gtatgtacaa tagaaggtgg    360
gtatatcgtt tccttcatat ggccattctg cccttctaca ttttgttggg ggtctaccga    420
agcacttctc agaatcctac tgtataaaat tatttcgaat caaagccccta agcctctcgt    480
atgcttcttc tagttactct catagtctca ttgtcgttac atgccgacac tttggatctt    540
ccatcctctt aagcaaacaa tactaccatt tttgcaagag aaaagaatca tcttcttccc    600
ggacaaggac gaatgagctg ggacgtggcg accggacgc gccactggct tcagaggccc    660
ggccccccta gtcggcagcc acctgccgac cactgatgcg accacacgta gctcccagcc    720
gcggcgattc gtccatctga ccagccctct ttatgggcta gtcggcactc acctgcccat    780
ccactcacga gcgcgcacgt cgtggttcgt atacctcca acggcctata atactgcgt    840
cgcgctgcat atgctttaca caaccacctg cttcacacta ccaaggcaag tacacagcag    900
caatacgtag tagatttccc gagtgaggag ctcagcgcaa gatg                      944
```

<210> SEQ ID NO 2
<211> LENGTH: 7
<212> TYPE: DNA
<213> ORGANISM: Triticum aestivum

<400> SEQUENCE: 2 cacctgc                                                             7

<210> SEQ ID NO 3
<211> LENGTH: 6
<212> TYPE: DNA
<213> ORGANISM: Triticum aestivum
<220> FEATURE:
<221> NAME/KEY: 5'UTR
<222> LOCATION: (3)..(4)
<223> OTHER INFORMATION: n is g, a, t or c

<400> SEQUENCE: 3 canntg                                                              6

<210> SEQ ID NO 4
<211> LENGTH: 7
<212> TYPE: DNA
<213> ORGANISM: Triticum aestivum

<400> SEQUENCE: 4 cactcac                                                             7

```
<210> SEQ ID NO 5
<211> LENGTH: 5
<212> TYPE: DNA
<213> ORGANISM: Triticum aestivum

<400> SEQUENCE: 5 ccgac                                                                    5

<210> SEQ ID NO 6
<211> LENGTH: 6
<212> TYPE: DNA
<213> ORGANISM: Triticum aestivum

<400> SEQUENCE: 6 cgtcgg                                                                   6

<210> SEQ ID NO 7
<211> LENGTH: 7
<212> TYPE: DNA
<213> ORGANISM: Triticum aestivum

<400> SEQUENCE: 7 gggtata                                                                  7

<210> SEQ ID NO 8
<211> LENGTH: 7
<212> TYPE: DNA
<213> ORGANISM: Triticum aestivum

<400> SEQUENCE: 8 actacca                                                                  7

<210> SEQ ID NO 9
<211> LENGTH: 108
<212> TYPE: DNA
<213> ORGANISM: Triticum aestivum

<400> SEQUENCE: 9
gtcgcggcag aggcggcgtc ggacatcggg ccgttcacgt ccgcggtgtc ggacggggac        60
ggtgagatgc ggtgtcgaac gtcgggccgt tcacgtccgc gtcgtcgg                    108

<210> SEQ ID NO 10
<211> LENGTH: 6
<212> TYPE: DNA
<213> ORGANISM: Triticum aestivum

<400> SEQUENCE: 10 acgtcc                                                                   6

<210> SEQ ID NO 11
<211> LENGTH: 6
<212> TYPE: DNA
<213> ORGANISM: Triticum aestivum

<400> SEQUENCE: 11 gccgac                                                                   6

<210> SEQ ID NO 12
<211> LENGTH: 23
<212> TYPE: DNA
<213> ORGANISM: Triticum aestivum

<400> SEQUENCE: 12
```

```
cagccctctt tatgggctag tcg                                          23

<210> SEQ ID NO 13
<211> LENGTH: 24
<212> TYPE: DNA
<213> ORGANISM: Triticum aestivum

<400> SEQUENCE: 13
tgtgtacttg ccttggtagt gtga                                         24

<210> SEQ ID NO 14
<211> LENGTH: 20
<212> TYPE: DNA
<213> ORGANISM: Triticum aestivum

<400> SEQUENCE: 14
cctagtcggc agccacctgc                                              20

<210> SEQ ID NO 15
<211> LENGTH: 23
<212> TYPE: DNA
<213> ORGANISM: Triticum aestivum

<400> SEQUENCE: 15
cgactagccc ataaagaggg ctg                                          23

<210> SEQ ID NO 16
<211> LENGTH: 20
<212> TYPE: DNA
<213> ORGANISM: Triticum aestivum

<400> SEQUENCE: 16
atgccgacac tttggatctt                                              20

<210> SEQ ID NO 17
<211> LENGTH: 20
<212> TYPE: DNA
<213> ORGANISM: Triticum aestivum

<400> SEQUENCE: 17
gcaggtggct gccgactagg                                              20

<210> SEQ ID NO 18
<211> LENGTH: 20
<212> TYPE: DNA
<213> ORGANISM: Triticum aestivum

<400> SEQUENCE: 18
gcacttctca gaatcctact                                              20

<210> SEQ ID NO 19
<211> LENGTH: 20
<212> TYPE: DNA
<213> ORGANISM: Triticum aestivum

<400> SEQUENCE: 19
aagatccaaa gtgtcggcat                                              20

<210> SEQ ID NO 20
<211> LENGTH: 23
<212> TYPE: DNA
<213> ORGANISM: Triticum aestivum

<400> SEQUENCE: 20
```

-continued

```
tttgcatccg cgcgggtata cgt                                              23

<210> SEQ ID NO 21
<211> LENGTH: 21
<212> TYPE: DNA
<213> ORGANISM: Triticum aestivum

<400> SEQUENCE: 21
tgagaagtgc ttcggtagac c                                                21

<210> SEQ ID NO 22
<211> LENGTH: 22
<212> TYPE: DNA
<213> ORGANISM: Triticum aestivum

<400> SEQUENCE: 22
ttgggacggc ggcgatcggc ca                                               22

<210> SEQ ID NO 23
<211> LENGTH: 23
<212> TYPE: DNA
<213> ORGANISM: Triticum aestivum

<400> SEQUENCE: 23
acgtataccc gcgcggatgc aaa                                              23
```

LOW TEMPERATURE-INDUCIBLE WHEAT WCS120 GENE PROMOTER

FIELD OF THE INVENTION

The present invention relates to the identification and characterization of a promoter of the wheat wcs120 gene. This promoter is inducible by low temperatures in both moncotyledoneous and dicotyledoneous species. It can therefore be used as a universal promoter for genes that are involved in the improvement of low temperature or freeze tolerance in plants.

BACKGROUND OF THE INVENTION

During the exposure of plants to low temperature (LT), and in the process of cold acclimation (CA) of plants, many physiological and biochemical changes occur, leading in some plants to the development of freezing tolerance (FT). The survival of these tolerant plants at freezing temperatures depends on the timely modulation of specific sets of genes, for which the accumulation of both mRNA and encoded proteins correlate with the development of FT (Guy, C. L. (1990) Annu. Rev. Plant Physiol. Plant Mol. Biol. 41: 187–223; Thomashow, M. F. (1990) Adv. Genet. 28: 99–131). A cryoprotective function has been proposed for several low temperature-responsive genes (Houde, M., et al. (1995) Plant J. 8: 583–593; Kurkela, S., et al. (1990) Plant Mol. Biol. 15: 137–144; Sieg, F., et al. (1996) Plant. Physiol. 111:215–221).

The molecular mechanisms governing gene expression at low temperature are not well understood. Recent reports suggest a role for calcium as second messenger in the early events following exposure to chilling temperatures (Knight, H., et al. (1996) Plant Cell 8:489–503; Monroy, A. F., et al. (1995) Plant Cell 7: 321–331). The $Ca^{2+}$ signal is likely transduced in a series of phosphorylation events which may involve $Ca^{2+}$-dependent protein kinases. However, there is little information regarding the downstream signalling components leading to the activation of specific sets of genes in response to LT.

Few cis-acting elements responsive to low temperature have been identified so far. In the case of the cor15a gene of *Arabidopsis thaliana,* Baker, S. S., et al. ((1994) Plant Mol. Biol. 24:701–713) suggested a potential role of G-box-like elements in ABA (abscissic acid) and drought responsiveness. However it is unclear whether these elements also play a role in LT responsiveness. The DR1 core motif (TACCGACAT) in the promoter of the *A. thaliana* rd29A gene is a cis-element implicated in the response to dehydration, high salt and low temperature (Yamaguchi-Shinozaki. K., et al. (1994) Plant Cell 6:251–264). A similar low-temperature regulatory element (LTRE)(TGGCCGAC), found in the promoter of the *Brassica napus* BN115 gene, contains the pentamer CCGAC motif which imparts low-temperature responsiveness (White, T. C., et al. (1994b) Plant Physiol. 106:917–928); Jiang, C., et al. (1996) Plant Mol. Biol. 30: 679–684). This motif or similar variants is also present in the promoters of cor15a (Baker, S. S., supra), rd29A (Yamaguchi-Shinozaki, K., supra), Iti78 and Iti65 Arabidopsis genes (Nordin K., et al. (1993) Plant Mol. Biol. 21:641–653) and blt4.6 and blt4.9 barley genes (White A. J, et al. (1994a) J. Exp. Bot. 45:1885–1892).

Several LT-responsive cDNA clones from wheat have been characterized. Among these, the Wcs120 gene is specifically regulated by low temperature (Houde M., et al. (1992) Plant Physiol. 99:1381–1387). The encoded 50 kDa protein is the major member of the WCS120 protein family (Houde, M. (1995), supra). Southern analysis indicates that the gene copy number and gene organization are identical in both freezing tolerant and sensitive wheat cultivars. On the other hand, the accumulation of both Wcs120 mRNA and encoded protein is shown to correlate closely with the differential capacity of wheat cultivars to develop FT (Limin, A. E., et al. (1995) Genome 38:1023–1031). Homologs of Wcs120 and other cold-regulated genes are present in chilling sensitive Gramineae species such as rice and corn, but they are not induced by low temperature (Danyluk, J., et al. (1994) FEBS Lett. 344:20–24). It appears that the expression of the wcs120 gene is regulated mainly at the transcriptional level. It is possible that the inability of some species to CA and to develop FT is due to inefficient cis-acting elements in the promoter or the absence of LT-specific transcription factors.

There thus remains a need to identify the nuclear events regulating the cold-specific expression of the Wcs120 gene. It therefore appeared of great interest to characterize the promoter region of the wheat wcs120 gene and to analyse the role of the promoter in the development of FT in plants.

The present invention seeks to meet these and other needs.

SUMMARY OF THE INVENTION

The invention concerns the identification of nuclear events regulating cold-specific gene expression involved in CA of plants in the development of FT. Specifically, it is the characterization of a gene promoter in plants that is induced in response to low temperature to express genes involved in the CA of plants. The promoter of this invention was first isolated from the 5' start site of the wheat wcs120 gene, sequenced and analysed for specific elements or motifs. A comparison of homologous function in promoters in other genes that are expressed in response to adverse environmental conditions, in the same and different species has shown conservation of some of these motifs. Further, by deletion analyses of the promoter, the functions of specific promoter regions are characterized and their importance in the response to the development of FT is identified. The invention additionally teaches the ability of the promoter to be used as a universal promoter in driving genes in response to low temperature involved in CA in dicots and monocot plant species for improvement of FT.

The invention additionally relates to the nuclear factors and events involved in the expression of the wheat low-temperature responsive gene wcs120. The results demonstrate that these nuclear factors regulate the expression of wcs120 at the level of the promoter by differential binding of these factors to the promoter under different environmental conditions.

The inventors are the first to isolate, identify, sequence and characterize the promoter of the wheat wcs120 gene. The inventors are also the first to characterize the promoter and functional variants, fragments and derivatives thereof by deletion analyses.

The inventors are the first to demonstrate that this promoter can be induced by low-temperatures in all plants, those that are cold-sensitive and cold-tolerant, and, in monocot and dicots plant species, thus demonstrating the universality of the promoter in inducing homologous and heterologous gene expression in response to low temperature.

The inventors are also the first to demonstrate the role of nuclear factors in regulating the transcription of the wheat wcs120 gene in response to different temperatures.

Before the present invention, it was believed that sensitivity to low temperature and inability to CA in plants was due to genetic variability in the low temperature responsive genes. The inventors are the first to demonstrate that the level of repression of the cold-induced genes, specifically wcs 120, is not due to variations in the gene itself or its promoter but rather to nuclear factors acting at the level of the promoter.

The promoter of the present invention and any derivatives or fragments thereof, can therefore be used in the design of transgenic plants in need of improving resistance to low temperatures. This can be accomplished by replacing the homologous promoter with the promoter of the present invention or any derivatives or fragments thereof, to drive the expression of the genes needed to cold-acclimate a plant and in this manner improve the FT of the plant.

In accordance with the present invention, there is therefore provided, a sequence of the promoter region of the wheat wcs120 gene.

In accordance with another aspect of the present invention, there is also provided the promoter, derivatives or fragments thereof being universal, such that the promoter, derivatives or fragments thereof are capable of driving the expression of genes in response to low temperature in plants including, monocot and dicots, and, cold-sensitive and cold-tolerant species.

In accordance with another aspect of the present invention, there is provided, a use for the promoter of the instant invention in transgenic plants, monocot and dicots plant species, such that the construct comprises the promoter, derivatives or fragments thereof to drive the expression of genes in response to low temperatures in different plant species.

In accordance with yet another aspect of the present invention, there are provided elements within the promoter that have homologies with other promoter elements from other genes. There is also provided regions of the promoter that are the minimal size fragments, derivatives or variants thereof capable of responsiveness to low temperature.

The sequences and polypeptides useful to practice the invention include without being limited thereto, mutants, homologs, subtypes, alleles and the like. It shall be understood that generally, the sequences of the present invention should encode a functional catalytic and interaction domain. It will be clear to the person of ordinary skill that whether an interaction or catalytic domain of the present invention, variant, derivative, or fragment thereof retains its function can be readily determined by using the teachings and assays of the present invention and the general teachings of the art.

As used herein, the designation "variant" denotes, in the context of a variant of a sequence whether a nucleic acid or amino acid sequence, a molecule that retains a biological activity (either function or structural) that is substantially similar to that of the original sequence. This variant or equivalent may be from the same or different species and may be a natural variant or be prepared synthetically. Such variants include amino acid sequences having substitutions, deletions, or additions of one or more amino acids, provided that the biological activity of the protein is conserved. The same applies to variants of nucleic acid sequences which can have substitutions, deletions or additions of one or more nucleotides, provided that the biological activity of the sequence is generally maintained. When relating to a protein sequence, the substituting amino acid as chemico-physical properties which are similar to that of the substituted amino acid. The similar chemico-physical properties include, similarities in charge, bulkiness, hydrophobicity, hydrophylicity and the like.

The term "derivative" is intended to include any of the above described variants that have been used for the purpose of labelling, binding or are comprised in fusion product(s).

The term "fragment" refers to any segment of an identified DNA, RNA or amino acid sequence and/or any segment of any of the variants or derivatives described in the above definitions.

Thus, the term "variant" refers herein to a protein or nucleic acid molecule which is substantially similar in structure and biological activity to the protein or nucleic acid of the present invention.

The terms "variants", "derivatives" and "fragments" of the present invention refer herein to proteins or nucleic acid molecules which can be isolated/purified, synthesized chemically or produced through recombinant DNA technology. All these methods are well known in the art.

Other objects, advantages and features of the present invention will become more apparent upon reading of the following non-restrictive description of preferred embodiments with reference to the accompanying drawing which is exemplary and should not be interpreted as limiting the scope of the present invention.

BRIEF DESCRIPTION OF THE DRAWINGS

FIG. 1a) Nucleotide sequence of the promoter of the low-temperature-responsive Wcs120 wheat gene (SEQ ID NO:1). The region corresponding to the mRNA is shown in lower case letters until the translation initiation ATG codon. The TATA box is located at −34 bp. The repeated motifs and putative cis-elements are underlined and described in the text.

FIG. 1b) Determination of the mRNA transcription start site. Lanes A, C, G, T, sequencing reaction performed using the same primer used for extension analysis. Lane X, extension products. The longest extension product is indicated with an arrow and was assigned a +1 value. The corresponding transcription start site is shown in bold in the nucleotide sequence of the coding strand.

FIGS. 9. a) and b) Deletion analysis of the wcs120 promoter by transient expression. (A) Schematic representation of the promoter fragments and relative positions of the repeated DNA motifs deduced from the sequence analysis (Genbank accession number AF031235). The constructions were named according to the first (5' deletions) or last (3' deletion) nucleotide of the promoter fragment. (B) Effect of cold treatment on the activity of the wcs120 promoter fragments. The leaf sections were transformed with the different promoter-luc fragments and Ubi-gus (pAHC27), and incubated at 4° C. for 3 days or at 24° C. for 2 days. Soluble proteins were extracted and enzymatic activities of LUC and GUS were determined. Numbers at the right of the error bars indicate the induction factors (4° C./24° C. relative activity ratio).

DESCRIPTION OF THE INVENTION

Figure 2:
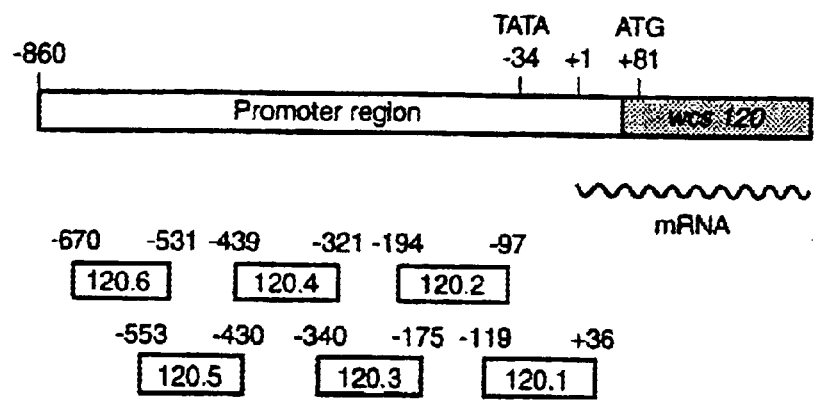
FIG. 2 Schematic representation of the Wcs120 promoter region. The map shows the relative position of the six overlapping promoter fragments used as probes in EMSA and southwestern experiments. Positions of the different elements are indicated relative to the transcription initiation start site (+1).

1. Identification and Characterization of the Promoter of the Wheat Wcs120 Gene and the Regulatory Mechanism for its Expression 1.1 Plant Material and Growth Conditions Winter wheat (*Triticum aestivum* L. cv Fredrick) was grown under controlled environment. Seeds were germinated for 5 days at 24/20° C. (day/night) in a mixture of vermiculite, soil and peat. Non-acclimated seedlings were kept at 24° C. for 10 days, while those treated for cold acclimation were transferred to 4/2° C. (day/night) for 20 days. Leaves were collected at the end of the indicated growth period and immediately used for nuclei extraction.

1.2 Identification of the Wcs120 promoter

The Wcs120 cDNA (Houde, M. (1992), supra) was used as a probe to isolate the corresponding genomic clone from a wheat genomic library (Clontech). The promoter region of the gene, identified by Southern analysis, was subcloned into pBluescript vector (Stratagene) and the nucleotide sequence was determined using the T7 sequencing kit (Pharmacia). Primer extension analysis was performed following the procedure of Ausubel, F. M., et al. (1992) In Short protocols in molecular biology, 2nd ed. Greene Publishing Associates & John Wiley & Sons, New York. Transient expression experiments were performed by microprojectile bombardment of wheat leaves using a construct bearing a transcriptional fusion of the full length promoter with the luciferase reporter gene. Cotransformation with a vector bearing the glucuronidase gene (GUS) driven by the ubiquitin promoter pAHC27 (Christensen, A. H., et al. (1996) Transgenic Res. 5:213–218) allowed standardization for the inherent variable transformation efficiency. Luciferase activity was determined using the Luciferase Assay System (Promega) and β-glucuronidase activity was determined according to Jefferson, R. A., et al. ((1987) EMBO J. 6:3901–3907).

1.3 Nuclei Isolation and Preparation of Nuclear Protein Extracts

Nuclei were isolated and purified from leaves using a modified procedure described by Nagao, R. T., et al. ((1981) DNA 1:1–9). All manipulations were carried out at 4° C. Briefly, 50 g of leaves were ground with a waring blender in 200 ml of homogenization buffer (1× basal buffer [25 mM MES pH 6.0, 10 mM $MgCl_2$, 1 mM $CaCl_2$, 20 mM KCl, 25 mM NaCl, 0.1% β-mercaptoethanol], 40% glycerol, 0.6 M sucrose). After filtration through 4 layers of cheese cloth, the filtrate was centrifuged for 20 min at 2,000× g. The pellets were gently resuspended in 50 ml of 'W' buffer (1× basal buffer, 25% glycerol, 0.5 M sucrose, 0.01% Triton X-100) and recentrifuged. The resulting pellets were resuspended in 10 ml of 'G' buffer (1× basal buffer, 0.5 M sucrose, 0.001% Triton X-100) and loaded on two discontinuous percoll gradients (80%, 50%, 35%, 22.5% and 15% percoll, prepared in 'G' buffer) and centrifuged for 30 min at 6,000×g. The banded nuclei at the 80/50% percoll interphase were collected, washed with 2 volumes of 'G' buffer and centrifuged for 20 min at 5,000×g. The purified nuclei were gently and thoroughly disrupted with a pestle in 6 ml of lysis buffer (20 mM HEPES-KOH pH 7.6, 420 mM NaCl, 20% glycerol, 0.5 mM DTT, 0.2 mM EDTA, 0.5 mM PMSF, 15 mg/ml leupeptin) (Allen, R. D., et al. (1989) Plant Cell 1:623–631) and centrifuged for 30 min at 100,000×g. The proteins in the supernatant were precipitated overnight on ice with the addition of solid ammonium sulfate (80% saturation). After centrifugation for 30 min at 100,000×g, the nuclear proteins were resuspended in 500 ml of dialysis buffer (20 mM HEPES-KOH pH 7.8, 50 mM KCl, 20% glycerol, 0.5 mM DTT, 0.2 mM EDTA, 0.5 mM PMSF, 15 mg/ml leupeptin) (Allen, R. D., supra), and dialyzed against the same buffer for 5 hours. These nuclear extracts (8–10 mg/ml protein) were stored frozen in small aliquots at −80° C.

1.4 DNA Probes and Electrophoretic Mobility Shift Assay (EMSA)

Oligonucleotides were synthesized with a Gene Assembler Plus DNA synthesizer (Pharmacia LKB) and purified on polyacrylamide-urea gels. The DNA primers were used to amplify overlapping fragments of the Wcs120 promoter: for fragment 120.1, CAGCCCTCTTTATGGGCTAGTCG (SEQ ID NO. 12) and TGTGTACTTGCCTTGGTAGT-GTGA (SEQ ID NO. 13) for upstream and downstream, respectively; fragment 120.2, CCTAGTCGGCAGCCAC-CTGC (SEQ ID NO. 14) and CGACTAGCC CATAAA-GAGGGCTG (SEQ ID NO. 15); fragment 120.3, ATGC-CGACAC TTTGGATCTT (SEQ ID NO. 16) and GCAGGTGGCTGCCGACTAGG (SEQ ID NO. 17); fragment 120.4, GCACTTCTCAGAATCCTACT (SEQ ID NO. 18) and AAGATCCAAAGTGTCGGCAT (SEQ ID NO. 19); fragment 120.5, TTTGCATCCGCGCGGGTATACGT (SEQ ID NO. 20) and TGAGAAGTGCTTCGGTAGACC (SEQ ID NO. 21); fragment 120.6, TTGGGACGGCGGC-GATCGGCCA (SEQ ID NO. 22) and ACGTATACC CGCGCGGATGCAAA (SEQ ID NO. 23). The PCR-amplified fragments were subcloned into pBluescript (Stratagene). Plasmids were isolated and the nucleotide sequences confirmed by dideoxy sequencing using the T7 Sequencing kit (Pharmacia). For the EMSA and southwestern analyses, the promoter fragments were radiolabelled by including 2.5 $\mu$Ci each of [$\alpha$-$^{32}$P]dCTP and [$\alpha$-$^{32}$P]TTP to the PCR reaction, and then purified on agarose gels. Protein-DNA binding reactions were performed essentially as described by Harter, K., et al. ((1994) Plant Cell 6: 545–559). The 20 $\mu$l mixture, containing 5 to 15 $\mu$g of nuclear proteins and 3 $\mu$g of double-stranded poly(dI-dC) as nonspecific competitor (Pharmacia), were preincubated for 10 min at 4° C. The DNA probe (50,000 cpm) was added and the mixture incubated for 20 min at 4° C. Competition experiments were performed under identical conditions by including unlabelled competitor fragments in the binding reaction prior to the addition of probe. For the dephosphorylation and phosphorylation treatments, the nuclear extracts were preincubated at 28° C. for 30 min with 1 unit of immobilized alkaline phosphatase (Sigma), or with 5 mM ATP and 2 mM sodium metavanadate (a phosphatase inhibitor) before the addition of the probes. The DNA-protein complexes were resolved on a 4% polyacrylamide gel prepared in TCE buffer (10 mM Tris-HCl pH 7.9, 3 mM sodium citrate, 1 mM EDTA) containing 8% glycerol, after a 1 h prerun at 180 V. Electrophoresis was carried out for 3 h at the same voltage in TCE buffer at 4° C. (Ausubel, F. M., supra) Gels were dried and exposed to X-ray films at −80° C.

1.5 Southwestern Assay

Nuclear proteins (15 $\mu$g) from NA and CA plants were either phosphorylated or dephosphorylated as for the EMSA assays, separated by SDS-PAGE, and then blotted onto nitrocellulose membranes. For protein renaturation, the membranes were submerged in the binding buffer described by Harter, K., supra containing 6 M urea for 10 min and transferred sequentially to fresh binding buffer with decreasing concentrations of urea (3, 1.5 and 0.75 M) for 10 min each wash, followed by two final rinses in binding buffer alone. The membranes were blocked in binding buffer containing 5% non-fat dry milk for 30 min, briefly rinsed twice with binding buffer containing 0.25% non-fat dry milk, and incubated overnight at 4° C. without shaking in buffer (200 $\mu$l/cm$^2$) containing 10 $\mu$g/ml sheared herring sperm DNA and radiolabelled probe (>10$^6$ cpm/ml). After three 5 min washes in cold binding buffer containing 0.25% non-fat milk, the membranes were exposed to X-ray film at −80° C.

1.6 Determination of Endogenous Kinase Activity

To determine the qualitative changes in the phosphorylation pattern following cold treatment, the nuclear extracts from both NA and CA plants (10 $\mu$g protein) were incubated for 5 to 40 min at 30° C. in binding buffer (Harter, K., supra) containing 1 mM MgCl$_2$, 50 $\mu$Ci [$\gamma$-$^{32}$P]ATP and 1 mM CaCl$_2$. At specified intervals, reactions were stopped by adding one volume of 2× SDS-sample buffer and the proteins were separated by SDS-PAGE. Gels were dried, exposed to X-ray film and the signal intensity of individual bands was determined by quantitative densitometry. To accurately quantify the Ca$^{2+}$-dependent and Ca$^{2+}$-independent nuclear kinase activities, the incorporation of $^{32}$P on histone III-S, casein or the PKC-specific substrate peptide MARCKS (Biomol; Blackshear, P. J. (1993) J. Biol. Chem. 268: 1501–1504) was determined as described elsewhere (Kitano, T., et al. (1986) Methods Enzymol. 124: 349–352). Histone III-S and casein are suitable substrates for phosphorylation assays, particularly when dealing with a crude mixture of uncharacterized protein kinases.

1.7 In vivo Okadaic Acid Treatment and Western Analyses

Wheat shoots were cut and immediately incubated in water or in the presence of the phosphatase inhibitor okadaic acid (OA) at 10, 100 or 1000 nM. The plants were left at room temperature for 4 hours to allow translocation of the inhibitor, then transferred to 4° C. for 24 hours, and the total soluble proteins were extracted as described (Limin, A. E., supra). For Western analysis, 10 $\mu$g of protein from total soluble extracts were separated by SDS-PAGE, electroblotted onto nitrocellulose membranes and probed with the anti-WCS120 antibody following procedures described previously (Houde, M. (1995), M., supra). The signal intensity for individual protein bands on the X-ray films was quantified with a Personal Densitometer SI (Molecular Dynamics) using the ImageQuaNT version 4.2 software. The results are presented as the integrated intensity of all the pixels in each band excluding the background. Similarly, the detection of PKC protein was done by Western analysis of total soluble extracts and nuclear extracts (10 mg proteins) from NA and CA plants, using individual mammalian (rabbit) polyclonal antibodies specific to isoforms $\alpha$, $\beta$, $\gamma$, $\delta$, $\epsilon$, and $\zeta$ of PKC (Boehringer Mannheim).

2. Deletion Analyses of the Promoter and Cold-Inducibility in Monocotyledonous and Dicotyledonous Species 2.1 Plant Material and Growth Conditions Seeds of winter (*Triticum aestivum* L. cv Fredrick) and spring wheat (*T. aestivum* L. cv Glenlea), barley (*Hordeum vulgare* L. cv Sophie) and winter rye (*Secale cereale* L. cv Puma) were germinated in moist vermiculite for 7 days. Control plants were maintained under controlled environment at a 24° C./20° C. (day/night) regime with a 15 h photoperiod and a 75% relative humidity. For rice (*Oryza sativa* L. cv Nipponbare), seeds were germinated in a water-saturated mixture of soil, peat and vermiculite at 28° C. with a 12 h photoperiod. Rapeseed (*Brassica napus* L. cv Jet Neuf), alfalfa (*Medicago sativa* ssp falcata L. cv Anik), sweet pepper (*Capsicum annuum* L. cv Superseft), cucumber (*Cucumis sativus* cv Vertige) and tomato (*Lycopersicon esculentum* Miller cv Floramerica) were grown at 24° C. in the same soil, peat and vermiculite mixture. For the cold treatment, plants were grown for one week with a 12 h photoperiod at 4° C. for wheat, barley, rye, alfalfa and rapeseed, or at 10° C. for rice, cucumber, pepper and tomato. Freezing tolerance of these species, expressed as the $LT_{50}$, varies as follows: rye (−25° C.), Fredrick wheat (−16° C.), Brassica (−16° C.), alfalfa (−15° C.), Glenlea wheat (−6° C.), barley (−4° C.), rice (4° C.), pepper, tomato and cucumber (5–10° C.).

2.2 Transient Expression Experiments

A deletion series of the 942 bp sequenced region, upstream of the ATG translation initiation codon of wcs120, was generated by exonuclease III and exonuclease VII digestion and the subclones were sequenced (T7 sequencing kit, Pharmacia). Constructions bearing transcriptional fusions of the promoter fragments with the luciferase reporter gene and the nos terminator were prepared in pBluescript. For the 3' deletions, the TATA box and transcription start site were provided by the 90 bp proximal fragment of the CaMV 35S promoter. Our results showed that, even though this promoter is much more efficient in dicots, it is active in wheat and its capacity to promote transcription is temperature independent (FIG. 10B, MIN). All the plasmids used were purified from *E. Coli* cultures by alkaline lysis and CsCl centrifugation.

For transformation, plasmid mixtures were prepared by mixing equal amounts of each wcs120 promoter-luciferase construct with a ubiquitin promoter-glucuronidase construct, pAHC27 (Christensen, A. H., supra). Plasmid DNA was coated on 0.9 µm tungsten beads (M-10, Bio-Rad) by ethanol precipitation (Godon, C., et al. (1993) Biochimie 75: 591–595) and delivered to the leaf tissues using a microprojectile bombardment apparatus (Vain, P., et al. (1993) Plant Cell Tiss. Org. 33: 237–246). The tissues were placed on an agar plate and bombarded with a 50 msec 85 PSI helium discharge under a vacuum of 25 inches of Hg. They were then floated on a nutrient solution (0.5 gl 20:20:20, N:P:K; CIL) in a Petri dish and incubated for 2 days at 24° C. or 3 days at 4° or 10° C., as specified for each experiment. Soluble proteins were extracted by grinding each sample (≈50–60 mg) with a mortar and pestle in 400 µl of ice-cold extraction buffer (50 mM Na-phosphate pH 7.0, 10 mM DTT, 0.1% Triton X-100, 10 mM EDTA) and centrifugation at 10000 g for 10 min. The supernatant was used directly for enzymatic determination of luciferase, LUC (assay kit from Promega) and β-glucuronidase, GUS (Jefferson, R. A., supra) activities.

In all cases the results are expressed as LUC to GUS ratios, and are means±S.D. of atcf least 4 independent extracts. Prior to LUC/GUS calculation for the 4° C. samples, we found that a correction of the GUS values was absolutely necessary since the GUS activity obtained at 4° C. was constantly 2–4 fold lower than the activity at 24° C. A correction factor was thus calculated for each construct by dividing the average GUS activity at 24° C. by the average activity at 4° C. The individual GUS values at 4° C. were then multiplied by this factor to obtain the corrected values used in the LUC/GUS calculation. If this correction had not been made, the activity of the promoter at LT would have been overestimated.

Though, few representative examples of vectors and hosts have been provided herein, any vector and any host capable of providing similar function and that are known to a person skilled in the art, are within the scope of this invention.

RESULTS

3. Identification and Characterization of the Promoter of the Wheat Wcs120 Gene and the Regulatory Mechanism for Its Expression 3.1 Characterization of the Wcs120 Promoter Region The 5' region of the Wcs120 gene, comprising 942 bp upstream from the ATG translation start site, was sequenced (FIG. 1a) and is set forth in SEQ ID NO. 1. The nucleotides in SEQ ID. NO.1 are numbered starting from 1 to 944. This numerotation corresponds to the nucleotide numbering of FIG. 1a which starts from −860 and ends at +84. Primer extension analysis revealed a transcription initiation start site 82 nucleotides upstream of the ATG codon (FIG. 1b). This nucleotide was assigned a +1 value and all the elements discussed in the text are numbered accordingly. The sequence analysis (FIG. 1a) showed a TATA box-like motif at position −34 and several repeated motifs were also found. The element as set forth in SEQ ID NO. 2, CACCTGC is repeated three times while the sequence as set forth in SEQ ID NO. 3, CANNTG is a consensus motif repeated 8 times. The core CANNTG motif is also present in the promoter region of many genes regulated by a variety of environmental and physiological stimuli, including light-regulated and ABA-responsive genes (Guiltinan, M. J., et al. (1990) Science 250:267–271; Williams, M. E., et al. (1992) Plant Cell 4: 485–496). This core sequence was identified as the preferred binding site for the common plant regulatory factors (CPRFs), the G-box binding factors (GBFs) belonging to the basic leucine zipper (bZIP) class of proteins, and for the b-HLH (basic helix-loop-helix) family of transcription factors proteins which play a key role in cell progression and developmental gene regulation (Anthony-Cahill, S. J., et al. (1992) Science 255:979–983; Davis, R. L., et al. (1990) Cell 60:733–746; Kusano, T., et al. (1995) Mol. Gen. Genet. 248:507–517; Harter, K., supra; Weisshaar, B., et al. (1991) EMBO J. 10:1777–1786). Another element, CACTCAC, as set forth in SEQ ID NO. 4, is repeated two times and has been identified as the recognition site for GCN4 and zeste factors, which play a direct role in enhancing gene transcription in yeast and Drosophila, respectively (Chen, J. D., et al. (1992) Mol. Cell Biol. 12:598–608; Thireos, G., et al. (1984) Proc. Natl. Acad. Sci. 81:5096–5100). Interestingly, the pentamer as set forth in SEQ ID NO. 5, CCGAC, reported to be essential in the low-temperature responsiveness of the BN115 gene from *Brassica napus* (Jiang, C., supra) is repeated two times in the Wcs120 promoter. Several other repeated elements are present but do not show significant homology to known motifs: the first, as set forth in SEQ ID NO. 6, CGTCGG, repeated 5 times, the second, as set forth in SEQ ID NO. 7, GGGTATA, 2 times, and the third, as set forth in SEQ ID NO. 8, ACTACCA, 2 times. There is also a major direct repeat, as set forth in SEQ ID NO. 9, and found between −810 and −703, which contains two 52 bp elements separated from each other by 4 bp. The core motif as set forth in SEQ ID NO. 10, ACGTCC, present in this repeat was reported to be recognized by mlip15, a bZIP protein induced by low temperature in maize (Kusano, T., supra). This observation opens up the possibility that a bZIP protein may be involved in Wcs120 gene regulation.

Sequence comparison between the Wcs120 promoter and those of several genes regulated by either low temperature, drought, salinity or ABA did not reveal significant homologous regions (Baker, S. S., supra; Ouellet, F., et al. (1994) Meeting Abstract, Annual Meeting of the Canadian Federation of Biological Societies. Montréal, Canada.; White, T. C. (1994b), supra; Yamaguchi-Shinozaki, K., supra), except in the case of the barley homolog Dhn5 (Close, T. J., et al. (1995) Plant Physiol. 107:289–290).

To confirm that the Wcs120 promoter is indeed responsive to low temperature, transient expression experiments were performed by microprojectile bombardment of wheat leaves using a construct bearing the full length promoter fused to the luciferase reporter gene. The results showed that luciferase activity was on average 8-fold higher in the transformed leaves exposed to 4° C. compared to the leaves maintained at 25° C. In contrast, the luciferase activity driven by the ubiquitin promoter did not increase at low temperature. The results of a complete transient expression analysis using different deletion constructs of the promoter are presented hereinbelow.

Figure 3:
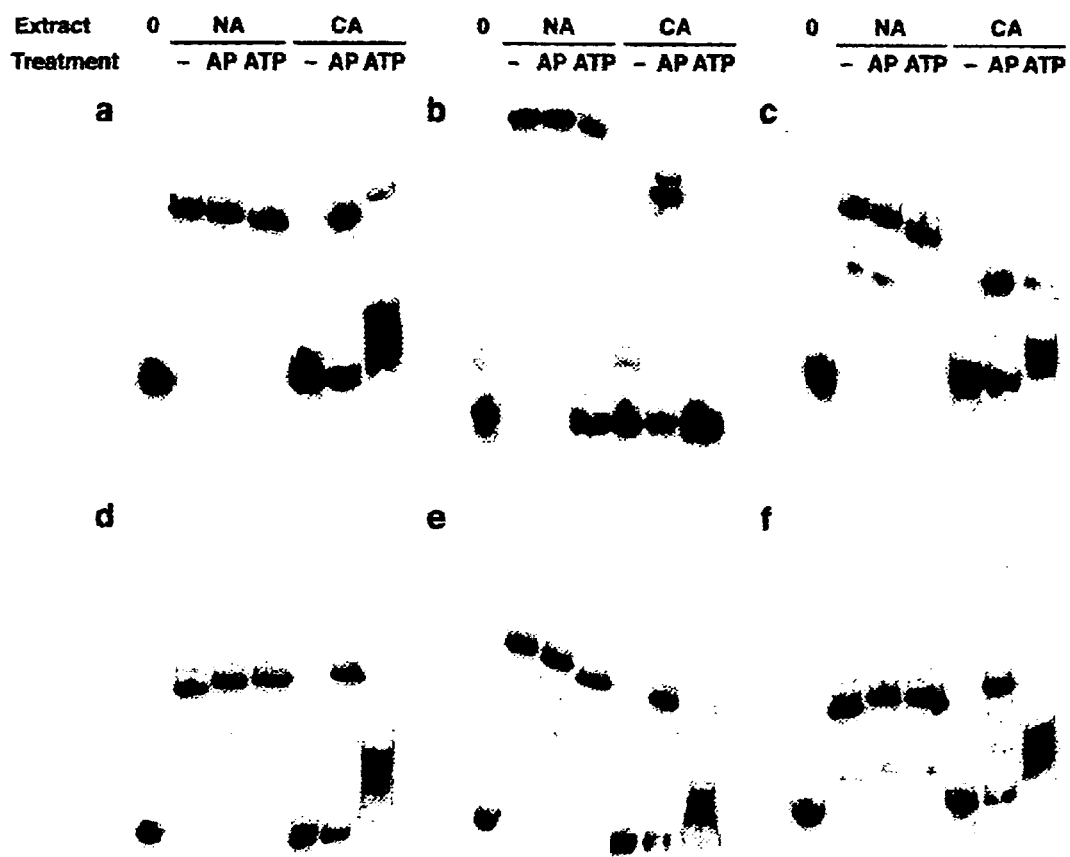
FIGS. 3. a) to f) Electrophoretic mobility shift assays showing the binding activity of Wcs120 promoter fragments with nuclear factors from non-acclimated (NA) and cold-acclimated (CA) extracts. The nuclear extracts (15 mg proteins) were preincubated in binding buffer alone (−), with immobilized alkaline phosphatase (AP) or with ATP and the phosphatase inhibitor sodium metavanadate (ATP). The $^{32}$P-labelled probes were added and the complexes were resolved on Tris-citrate-EDTA native polyacrylamide gels. Free probe (0). Position of the probes with respect to the promoter region is indicated in FIG. 2. a) probe 120.1; b) probe 120.2; c) probe 120.3; d) probe 120.4; e) probe 120.5; f) probe 120.6.

3.2 Nuclear Proteins from Non-Acclimated Plants Interact with Sequences of the Wcs120 Promoter In order to investigate the interactions of nuclear DNA-binding factors with elements in the Wcs120 promoter, six overlapping fragments (100–160 bp) spanning approximately 700 bp of the promoter region (FIG. 2) were amplified by PCR and used as probes in gel retardation experiments. DNA-protein complexes with different relative mobility were detected when the 6 fragments were incubated with nuclear extracts from NA plants (FIG. 3, NA, lanes "-"). These differences in mobility suggest that the binding proteins are of different size and/or that the DNA-protein complexes have different conformation. In spite of the presence of similar motifs (putative cis elements) in the different promoter fragments, competition experiments performed with non-labelled fragments indicated that the nuclear proteins bind each fragment in a specific manner. The differences in the relative mobility of the complexes and the specificity of the interactions indicate that the promoter region binds several and distinct nuclear proteins at normal growth temperature. In contrast, no detectable complexes were formed when the same probes were incubated with nuclear extracts from CA plants (FIG. 3, CA, lanes "-"). Lack of DNA-binding activity in the CA nuclear extracts is due to either, absence or in vivo inactivation of the nuclear DNA-binding factors during the acclimation of wheat plants at 4° C. This absence of binding of nuclear factors to the DNA of the promoter region provides the plant with the ability to CA.

3.3 In vitro Dephosphorylation Restores DNA-Binding Activity of Proteins in CA Extracts To better understand the differential pattern of DNA-protein interactions between NA and CA nuclear extracts, we performed experiments to test whether the binding factors are modulated by phosphorylation or dephosphorylation. The results in FIG. 3 (NA, lanes AP and ATP) show that in the NA extracts, the DNA-binding activities to all probes except 120.2 were not significantly affected by alkaline phosphatase (AP) nor ATP treatments. However, the ATP treatment inhibited partially the DNA-binding activity to fragment 120.2, observed as an accumulation of unbound probe (FIG. 3b, NA, lane ATP). In contrast, when the CA extracts were dephosphorylated with AP, most of the DNA-binding activities were restored (FIG. 3, CA, lanes AP). These reactivated nuclear factors produced complexes with similar or slightly different mobility to those observed in untreated NA extracts. In the case of the CA extracts treated with ATP and the phosphatase inhibitor Na-metavanadate, a partial restoration of binding was observed. This partial restoration could be the result of the phosphorylation of the nuclear factors by the active endogenous kinases, or by the incomplete inhibition of unknown phosphatases, or both. These results indicate that the DNA-binding factors in the nuclear extracts from NA plants are in a dephosphorylated state and probably interact in vivo with elements in this promoter at normal growth temperature. The inability of ATP to stimulate phosphorylation in the NA extracts (and inactivate the DNA-binding factors) may be due to the in vivo absence and/or inactivation of a particular protein kinase(s) in the nucleus at normal growth temperature. The data further suggests that preferential binding of these factors at normal temperatures produces a transcriptional repression of the Wcs120 promoter.

Figure 4:
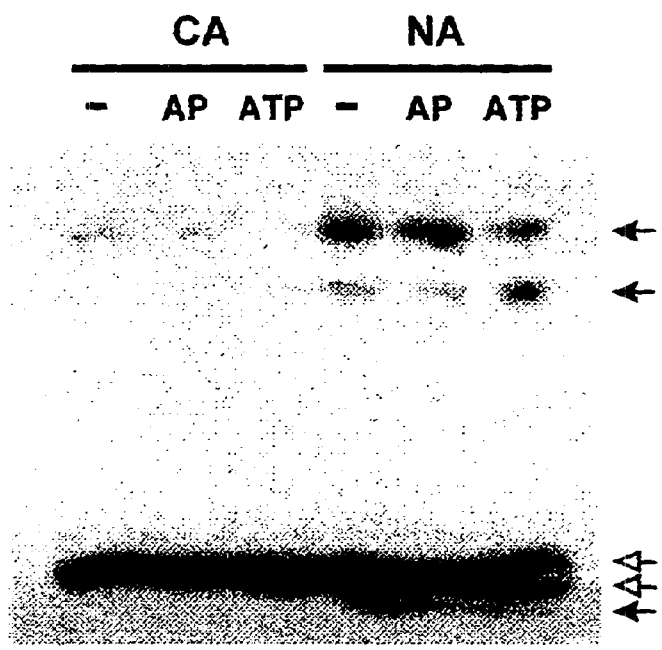
FIG. 4 Southwestern analysis showing the binding of nuclear proteins from non-acclimated (NA) and cold-acclimated (CA) plants with probe 120.4. The nuclear extracts (15 mg proteins) were pre-incubated in binding buffer (−), with alkaline phosphatase (AP) or with ATP and the phosphatase inhibitor sodium metavanadate (ATP). The proteins were separated by SDS-PAGE and transferred to nitrocellulose membranes. The proteins were then renatured by successive washes of decreasing concentrations of urea and incubated with the labelled probe. The membranes were washed and exposed to X-ray film.

To determine whether these DNA-binding factors regulated by protein kinases and phosphatases are homodimeric or heterodimeric in nature, southwestern analyses were performed. The results in FIG. 4 show that at least 5 distinct DNA-binding proteins in the NA extracts interact with elements present in fragment 120.4. Their binding capacity was not significantly modified by phosphorylation or dephosphorylation, as found in EMSA experiments (FIG. 4, NA, lanes AP and ATP). In the CA extracts, only two out of the five proteins did bind to the DNA probe, indicating that they may be unrelated to low-temperature regulation since proteins of similar molecular weight from both NA and CA extracts also bind to the other promoter fragments. Therefore, at least three DNA-binding proteins were absent or presumably inactivated in vivo during cold acclimation. The binding capacity in the CA extracts was not restored by in vitro AP pretreatment (FIG. 4, CA, lane AP). This is in contrast with the EMSA results (FIG. 3d) which clearly showed that dephosphorylation restores the DNA-binding activity. The probable cause is that under the conditions used, these factors did not renature to their active conformation. Southwestern allows the detection of primary DNA ligands or homodimeric proteins but not heterodimeric proteins. The phosphorylation target is probably a regulatory subunit(s) which is associated with DNA-binding subunits. Put together, this data indicates that the factors regulated by protein kinases and phosphatases as shown by EMSA are probably heterodimeric proteins. In support of this statement, it is well established that many DNA binding proteins of the bHLH and plant bZIP class of proteins selectively form DNA-binding heterodimers (Armstrong, G. A., et al. (1992) Plant Cell 4:525–537; Davis, R. L., supra).

Nuclear factors to the DNA of the wcs120 gene are modulated by phosphorylation/dephosphorylation of the nuclear factors. Nuclear factors are in a state of dephosphorylation for DNA binding. This DNA binding of these dephosphorylated nuclear factors produces transcriptional repression of the wcs120 gene promoter.

3.4 Nuclear Kinase Activity is Stimulated by Cold Acclimation

Figure 5:
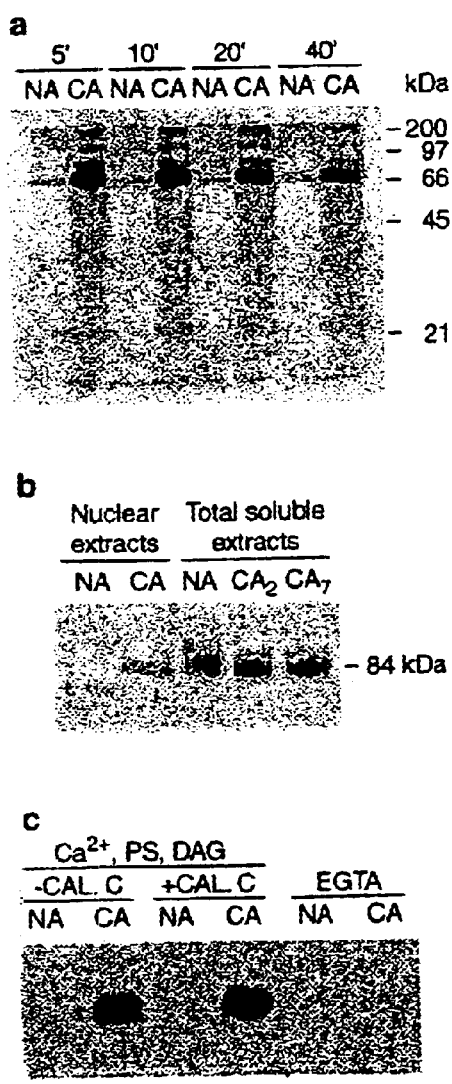
FIGS. 5. a) to c) Analysis of endogenous kinases in nuclear extracts from non-acclimated (NA) and cold-acclimated (CA) wheat plants. a) In vitro phosphorylation of nuclear proteins. Equal amounts of nuclear proteins (10 μg) were incubated with [γ-$^{32}$P]ATP and separated by SDS-PAGE. The gel was dried and exposed to a X-ray film. b) Immunodetection of a PKCg homolog in nuclear and soluble extracts from non-acclimated (NA) and cold-acclimated (CA) plants. Equal amounts of proteins (10 μg) were separated by SDS-PAGE, blotted onto nitrocellulose membranes and probed with the anti-PKCg antibody. CA2 and CA7 indicate soluble extracts from 2 and 7 days cold-acclimated plants. c) PKC activity was measured in the nuclear extracts with the peptide MARCKS as the PKC-specific substrate and containing the indicated chemicals. Calphostin C (CAL.C) and EGTA concentrations are 0.1 μM and 0.5 mM, respectively. Aliquotes of each reaction were separated by SDS-PAGE and visualized by autoradiography. PS, phosphatydylserine; DAG, diacylglycerol.
Figure 6:
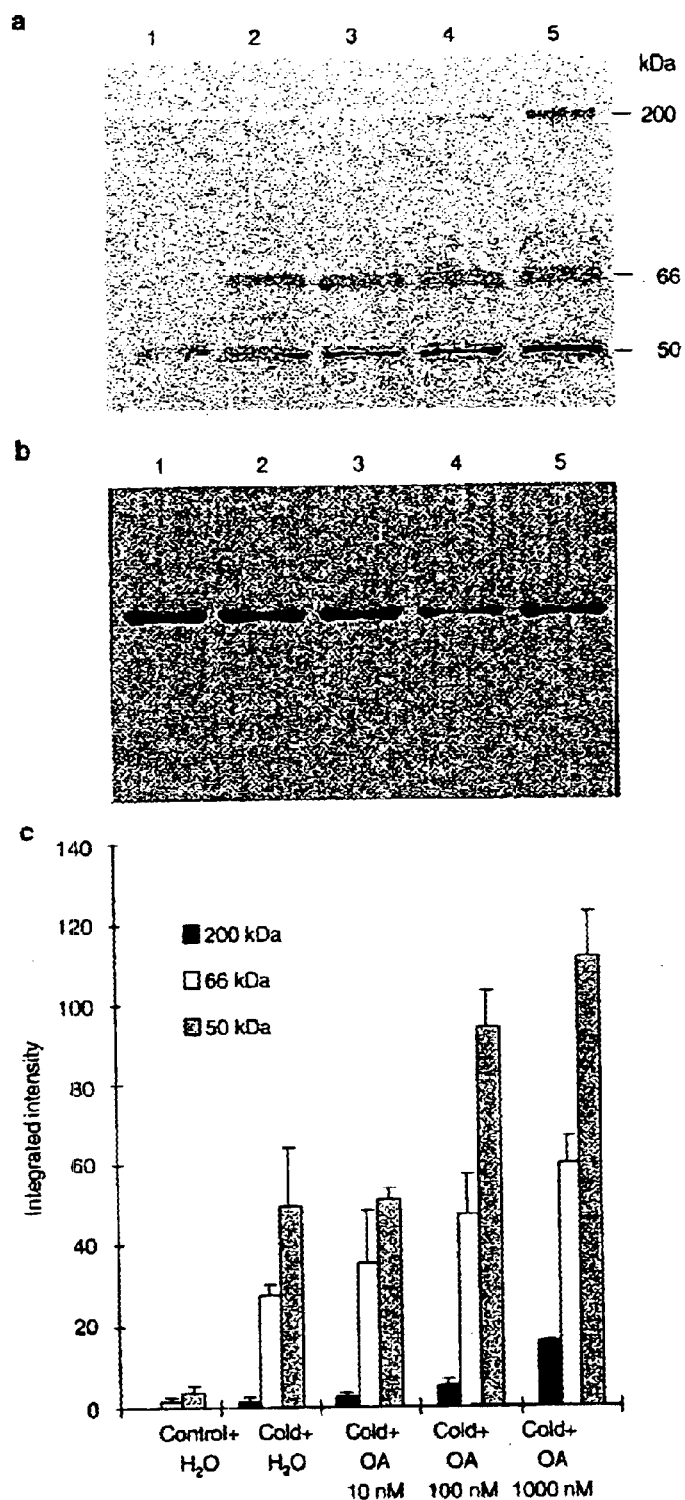
FIGS. 6. a) to c) Effect of in vivo okadaic acid treatment on the accumulation of the cold-inducible WCS120 family of proteins. Wheat seedlings were incubated at low temperature without or with different concentrations of okadaic acid (OA), and soluble proteins were extracted and separated by SDS-PAGE. a) Immunodetection of the WCS120 protein family in the soluble extracts. Following the treatment, the proteins were analyzed by western blot using the anti-WCS120 antibody. b) SDS-PAGE gel stained with Coomassie blue showing equal protein loading. c) Densitometric quantification of the individual protein bands of 50, 66 and 200 kDa of the immunoblot shown in a. The 50 kDa protein is encoded by Wcs120 gene. Values represent averages and standard deviations of the integrated intensity of the pixels for each protein band, excluding the background, from at least three independent experiments.

In order to find a correlative explanation of the differential phosphorylation state of the nuclear factors in the NA and CA extracts, endogenous kinase activity was determined. The results in FIG. 5a show that protein kinase activity was significantly higher in the nuclear CA extracts than in the NA extracts, with a major difference being the phosphorylation of a 24 kDa protein. Densitometric quantification showed that incorporation of $^{32}P$ was 6-fold higher in CA extracts compared to NA extracts. The possible implication of $Ca^{2+}$-dependent and $Ca^{2+}$-independent protein kinases in the phosphorylation of nuclear proteins was determined. The results in Table 1 show that the incorporated $^{32}$P onto histone catalyzed by both $Ca^{2+}$-independent and $Ca^{2+}$-dependent kinase activities was significantly higher in the CA extracts compared to the NA extracts. A similar increase in the incorporation of $^{32}$P onto casein catalyzed by $Ca^{2+}$-dependent kinase activity was observed in the CA extracts than in the NA extracts. Table 1, shows $Ca^{2+}$-independent and $Ca^{2+}$-dependent protein kinase activities in nuclear extracts from non-acclimated (NA) and cold-acclimated (CA) plants. The overall highly stimulated kinase activity in the CA extracts supports that the DNA-binding factors are inactivated by phosphorylation in vivo.

inhibitor of protein phosphatases PP1 and PP2A) (Smith, R. D., et al. (1996) Annu. Rev. Plant. Physiol. Plant. Mol. Biol. 47:101–125). Soluble proteins were extracted and the accumulation of the WCS120 family of proteins was analyzed by quantitative densitometry of western blots. The results showed an important increase in the levels of the 50, 66 and 200 kDa proteins at 4° C. (FIG. 6b, lane 2) compared to 25° C. (FIG. 6b, lane 1). When the plants were exposed to low temperature in the presence of several concentrations of OA (FIG. 6b, lanes 3, 4 and 5), accumulation of these proteins was significantly stimulated. At the highest concentration tested (1 $\mu$M), the densitometric analysis revealed a 2.2-fold increase of the 50 and 66 kDa proteins with respect to the

TABLE 1

| Protein substrate | $Ca^{2+}$-independent | | $Ca^{2+}$-dependent | |
| --- | --- | --- | --- | --- |
| | NA | CA | NA | CA |
| Histone III-S | 16034 ± 4703* | 29929 ± 2660* | 1236 ± 1618* | 10233 ± 3865* |
| Casein | 15186 ± 1223 | 17235 ± 758 | 14127 ± 1255* | 24494 ± 1331* |

Values are expressed as the $^{32}$P incorporated in CPM. Each data represent the (±S.E.) from three replicates. This experiment was repeated three times with results each time.
*Significance at P < 0.05, Student T.

3.5 Cold Acclimation Induces the Accumulation of a PKCg-like Protein in the Nucleus The highly stimulated kinase activity in the nuclear CA extracts may result from the activation and/or the translocation of cytoplasmic kinases into the nucleus when the plants are exposed to low temperature. To test this hypothesis, antibodies directed against six mammalian isoforms of protein kinase C (PKC) were used to detect wheat PKC homologs. A signal was obtained only with the anti-PKCg antibody, which cross-reacted with an 84 kDa protein (FIG. 5b). While this protein was equally abundant in the total protein extracts prepared from both NA and CA plants, its relative abundance in the nuclear CA extract was 22-fold higher than in the nuclear NA extract. To confirm this observation, the PKC-like activity was assayed in the nuclear extracts using the PKC-specific substrate peptide MARCKS (Blackshear, P. J., supra). The results in FIG. 5c show that the CA extracts phosphorylate the substrate at higher levels than the NA extracts. The protein kinase involved is stimulated by $Ca^{2+}$, PS and DAG, thus suggesting the presence of a PKC-like activity in the CA extracts. The addition of 0.5 mM EGTA resulted in only partial inhibition of the phosphorylation of MARCKS. This incomplete inhibition could be due to the insufficient chelation of $Ca^{2+}$ by EGTA under the standard experimental conditions used. The addition of Calphostin C at 0.1 mM, concentration at which mammalian PKC is inhibited (Lee, S. C., et al. (1996) J. Cell Biochem. 60:121–129), did not significantly inhibit the MARCKS phosphorylation. However, a complete inhibition of phosphorylation, as determined by $^{32}$P incorporation and scintillation counting, was obtained when 0.5 mM Calphostin C was added to the reaction. Together, these results indicate that during cold acclimation of wheat plants, a putative PKCg homolog is selectively translocated from the cytosol into the nucleus. This observation correlates with the increased $Ca^{2+}$-dependent kinase activity in the CA extracts.

3.6 Okadaic Acid Stimulates the Accumulation of the WCS120 Family of Proteins in Vivo To determine the role of protein phosphatases on the expression of Wcs120 gene, wheat seedlings were incubated at 4° C. in the presence of okadaic acid (a potent and specific plants exposed to low temperature without inhibitor (FIG. 6b, lane 2 and FIG. 6c). The stimulated accumulation of the 200 kDa protein was even more important, showing a 9-fold increase (FIG. 6c). These experiments suggest that, in vivo, the accumulation of the WCS120 protein family at low temperature is negatively regulated by PP1 and/or PP2A phosphatases, which compete for equilibrium with protein kinases on the state of phosphorylation of the putative repressor, and hence on their DNA-binding activity.

Our work provides evidence that several factors present in nuclear extracts from non-acclimated wheat plants interact with elements found in the promoter of the cold-inducible Wcs120 gene. Based on these results, we postulate that the regulation of Wcs120 gene expression in response to low temperature involves specific interactions of multiple nuclear factors. The preferential DNA-binding activity present in nuclear extracts from non-acclimated plants (24° C.) is thought to repress gene transcription. Conversely, when the plants are exposed to low temperature (4° C.) for cold acclimation, the nuclear factors become inactivated allowing transcription to take place. This temperature-dependent pattern of transcriptional activation/repression suggests the participation of nuclear proteins whose DNA-binding activity may be modulated by post-translational modifications such as phosphorylation (Clark A. R., et al., (1993) Biochem. J. 296:521–541; Hunter T., et al., (1992) Cell 70:375–387).

The mobility shift assays performed with different promoter fragments showed that only proteins from the NA extracts produced DNA-protein complexes. In vitro dephosphorylation of the CA nuclear extracts restored the DNA-binding activity, suggesting that during in vivo cold acclimation of wheat, these factors are probably inactivated by phosphorylation. Indeed, both $Ca^{2+}$-dependent and $Ca^{2+}$-independent kinase activities were significantly higher in CA extracts than in NA extracts. This low temperature-stimulated kinase activity in the CA nuclear extracts may contribute to the phosphorylation of the putative repressors. In support of these observations, several studies have demonstrated that phosphorylation can negatively affect the binding of nuclear factors to DNA (Datta N., et al. (1989) Plant Cell 1:1069–1077; Hunter, T., supra; Tjaden G., et al.

(1994) Plant Cell 6:107–118). It has been reported that $Ca^{2+}$-dependent protein kinases may play a role in the signal transduction during the early events following exposure at low temperature (Knight, H., supra; Monroy, A. F., supra). Our analysis of the pattern of protein phosphorylation in both nuclear extracts suggests the participation of both $Ca^{2+}$-independent and $Ca^{2+}$-dependent protein kinases, which possibly became activated and/or were translocated into the nucleus in response to low temperature.

In this work, we determined that a PKCg homolog is present in similar abundance in the cytosol of both NA and CA plants but is selectively translocated into the nucleus in response to low temperature. Similarly, it was reported that PKCg may be activated and targeted to the nucleus in mammalian T-cells treated with the tumor-inducer phorbol ester (Avraham H., et al. (1994) Int. J. Oncology 5:237–241). Consistent with this observations, the CA nuclear extracts phosphorylated the PKC-specific substrate MARCKS at higher levels than the NA extracts in the presence of activators $Ca^{2+}$, PS and DAG. However, relatively high concentrations of Calphostin C were required to inhibit this PKC-like activity, which is in agreement with the observations reported by Subramaniam R., et al. ((1997) Plant Cell 9:653–664). Presumably the plant PKC is less sensitive to Calphostin C than the mammalian PKC. Indirect evidence showing the existence of a PKC homolog in plants has been published recently (Nanmori, T., et al. (1994) L. Biochem. Biophys. Res. Comm. 203:311–318; Subramaniam, R., supra; Xing, T., et al., (1996) Plant Cell 8:555–564).

The phosphorylation status of proteins is a reversible mechanism governed by opposite activities of protein kinases and phosphatases (Hunter, T., supra). Therefore, we expected that the in vivo inactivation of protein phosphatase activity would shift the equilibrium state of the putative repressors towards the phosphorylated state by the predominant protein kinase activity. This shift in phosphorylation would decrease the DNA-binding capacity of the repressors and hence inactivate them, as our EMSA experiments have suggested. The overall effect on gene regulation is expected to result in an increased accumulation of the 50 kDa WCS120 protein. Our in vivo experiments with okadaic acid, which specifically inhibits PP1 and PP2A phosphatases (Smith R. D., supra), support the data obtained from the EMSA experiments and suggest that PP1 and/or PP2A may act as negative regulators of Wcs120 gene expression.

Figure 7:
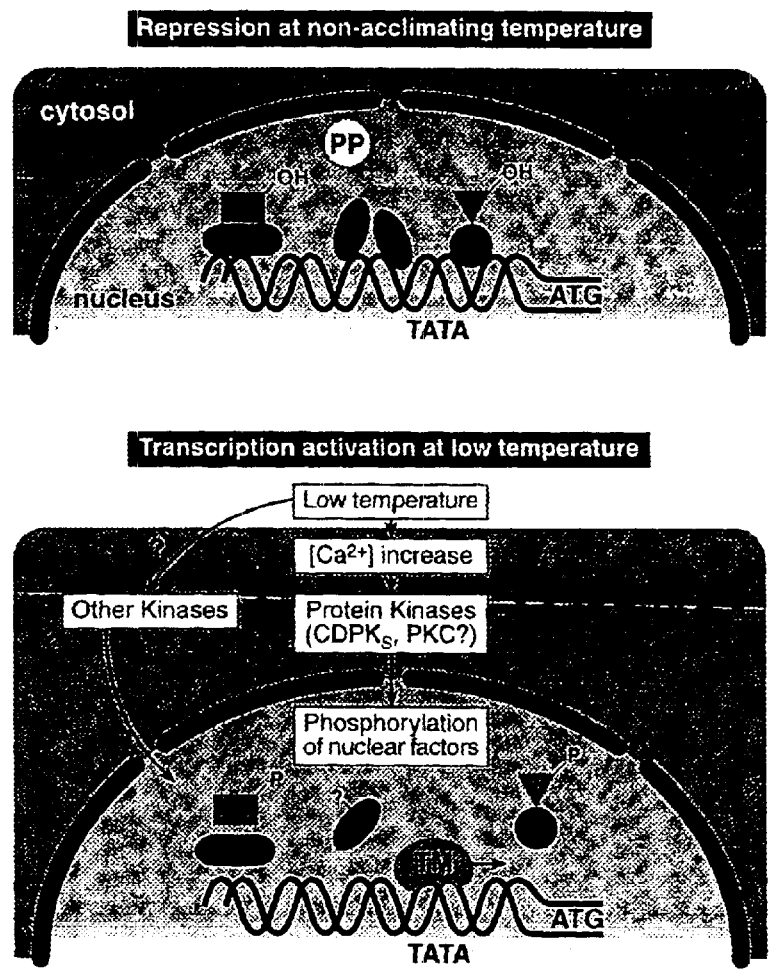
FIG. 7 Hypothetical model describing how temperature shifts regulate the expression of low-temperature-responsive genes.

The presence of multiple and distinct cis- and trans-acting elements suggests a complex mechanism of transcriptional regulation of the Wcs120 gene, such as those reported for light-regulated promoters (Schindler, U., et al. (1990) EMBO J. 9:3415–3427; Weisshaar B., supra). In the case of the CAB gene, Schindler, U., supra characterized five nuclear proteins involved in its light-mediated regulation. However, the authors observed that the DNA-binding factors were equally active in extracts from both dark- and light-adapted tobacco plants, thus preventing the establishment of a physiological relationship between in vitro DNA-binding activity and in vivo gene regulation. Similarly, the nuclear factors which interact with the DR1 motif (TACCGACAT) present in the promoter of the rd29A gene are active in extracts prepared from both high-salt-stressed and control plants (Yamaguchi-Shinozaki, K., supra). In contrast, our data provide strong evidence that the interaction of the nuclear repressors with the promoter of the low-temperature-responsive Wcs120 gene is regulated by a temperature shift. Although we suggest that repressor factors bind specifically to their cognate elements, we cannot rule out the possibility that positive transcription factors may also act as repressors (Davis R. L., supra; Sakamoto, A., et al. (1996) Plant Cell Physiol. 37:557–562). These factors may act as repressors by binding near or overlapping the binding site of the RNA polymerase complex, thus interfering with the assembly of the transcriptional machinery (Clark, A. R., supra; McBryant, S. J., et al. (1995) J. Mol. Biol. 250:315–326). Based on the data presented in this report, we propose in FIG. 7 a working model that describes the possible regulation of gene expression by low temperature. Under non-acclimated condition, protein phosphatases such as PP1 and/or PP2A maintain the putative repressors in a dephosphorylated state, which can thus bind actively to the Wcs120 promoter. The lower nuclear kinase activity at 25° C. (compared to 4° C.) suggests that some protein kinases are downregulated or absent from the nucleus. The repressor factors may interfere with the assembly of the general transcriptional machinery perhaps by overlapping near or at the site of the TATA box, resulting in the repression of Wcs120 expression. When the plant is exposed to low temperature, it is suggested that the signal is sensed and translated as an increase in cytosolic $Ca^{2+}$, leading to a series of phosphorylation events mediated by $Ca^{2+}$-dependent protein kinases. Our evidence indicates that a cytosolic PKCg homolog is selectively translocated into the nucleus during cold acclimation. The low temperature signal also up-regulates nuclear $Ca^{2+}$-independent kinases. We postulate that these low temperature-activated protein kinases phosphorylate and hence inactivate the repressor proteins, which are released from the promoter region. However, other post-translational modifications leading to the inactivation of DNA-binding factors cannot be ruled out. This derepression would allow the transcriptional machinery to assemble, thus activating gene transcription. Cloning and functional characterization of the transcription factors, PKC and the protein phosphatases regulating the expression of Wcs120 will help to understand this complex mechanism of regulation.

Figure 8:
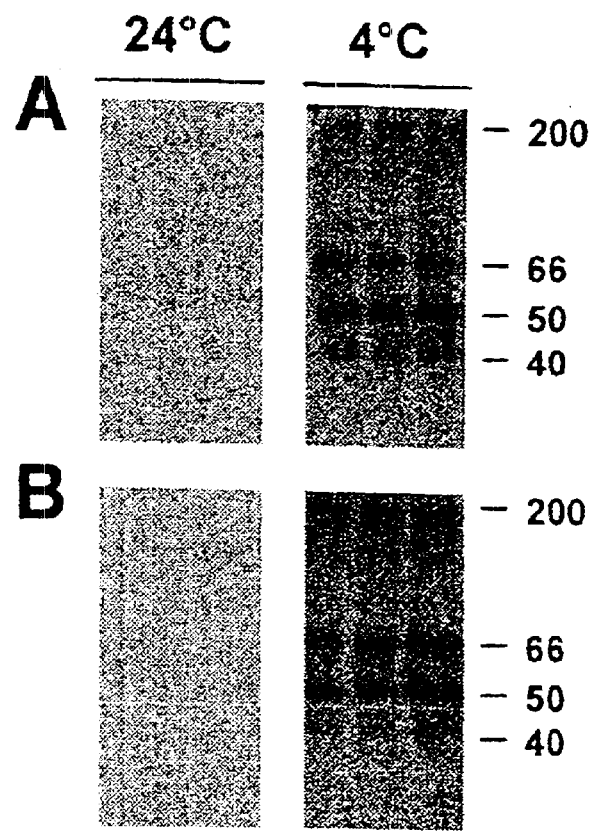
FIGS. 8. a) and b) Effect of bombardment on the expression of the endogenous WCS120 proteins. The proteins were extracted and analyzed by Western blotting using the polyclonal antibody directed against the members of the WCS120 family. Numbers on the right indicate the MW (in kDa) of the major members of the family. Three independent samples were analyzed for each condition. (A) Protein accumulation in non-transformed wheat leaves sections after 48 h at 24° C. and 72 h at 4° C. (B) Protein accumulation after bombardment of wheat leaves with tungsten beads without DNA and incubation at 24° C. for 48 h or at 4° C. for 72 h.

4. Deletion Analyses of the Promoter and Cold-Inducibility in Monocotyledonous and Dicolyledonous Species 4.1 Deletion Analysis Western analyses were performed to evaluate the capacity of the transformed tissues to express the endogenous wcs120 gene family upon LT exposure. The results show that the sections of untransformed leaves (FIG. 8A) and those of leaves transformed with the beads only (FIG. 8B) accumulate the WCS120 proteins in a similar manner. The conditions tested were those used for the post-bombardment incubation period in the transient expression assays. These results show that the wounding stress caused by the bombardment had no effect on the level of expression of the endogenous wcs120 genes, and should not affect the activity of the promoter in the transient assays.

Wheat leaves sections were transformed with constructs bearing the different deletions of the promoter transcriptionally fused to the luciferase (luc) reporter gene. The chimeric constructs are represented schematically in FIG. 9A. The results show that LT treatment increases LUC activity by 8-fold when the full length wcs120 promoter is used (FIG. 9B, FL860). A control experiment was performed using the pAHC18 (Ubi-luc) vector under the same conditions. The results showed no increase in LUC activity at 4° C. when the gene is driven by the Ubi promoter. This confirms that when the wcs120 promoter is used, the increase in activity observed at 4° C. is due to the LT-inducibility and not to an increased luc transcript stability at this temperature.

The 5' deletion up to −590 leads to an increase of the fold induction (FI) from 8 to 55-fold. This is mainly due to the almost complete loss of basal activity at 24° C. The region between −860 and −590 contains a 52 bp direct repeat composed of 2 elements separated from each other by 4 bp, and four of the five CGTCGG (SEQ ID NO. 6) elements which do not show any homology with known motifs. The loss of activity at both 4° and 24° C. upon deletion of this region suggests that either or both elements could act as transcriptional enhancers. It was reported that repeated sequences of 127 to 337 bp from Arabidopsis could act as enhancers in tobacco transgenic plants (Ott, R. W., et al. (1996) Mol. Gen. Genet. 252: 563–571). A further deletion to −415 increases the activity at both temperatures, suggesting that the region from −590 to −415 contains elements that repress transcription. This region contains the two GGG-TATA (SEQ ID NO. 7) elements of unknown function. The fact that the effect of the putative negative elements was not apparent in the FL860 construct suggests that the putative enhancers located between −860 and −590 may overcome or inactivate the negative factors of the −590 to −415 region. If the region between −415 and −215 is deleted, a decrease in activity is observed at both temperatures, suggesting the presence of enhancer elements. However, the significant decrease in activity at 4° C. suggests that this region could contain cold-inducible positive regulatory elements. In fact, this region contains a CCGAC (SEQ ID NO. 5) LTRE previously identified in the promoters of cor15A/rd29A from Arabidopsis and bn115 from Brassica napus (Baker, S. S., supra; Jiang, C., supra; Yamaguchi-Shinozaki, K., supra). The presence of a motif identical to this LTRE in the wcs120 promoter may suggest a similar role in wheat. A cDNA clone corresponding to a protein from Arabidopsis which can bind the CCGAC motif has been isolated recently (Stockinger, E. J., et al. (1997) P. Natl. Acad. Sci. 94:1035–1040).

The deletion of the region between −215 and −72 abolishes almost all promoter activity. The decrease of activity at 4° C. suggests that the deleted region contains a LTRE. This region contains the other GCCGAC (SEQ ID NO. 11) LTRE and 2 of the 3 CACCTGC (SEQ ID NO. 2) elements. The latter elements contain the CANNTG (SEQ ID NO. 3) motif, which forms the core of several cis-acting elements such as the ABA response elements (ABRE) (Meshi, T., et al. (1995) Plant Cell Physiol. 36: 1405–1420). This motif was identified as the preferred binding site for the bHLH proteins, the common plant regulatory factors (CPRFs) and for the G-box binding factors (GBFs) belonging to the bZIP class of proteins (Meshi, T. supra). Another element, CACTCAC (SEQ ID NO. 4), is repeated 2 times and was identified as a binding site for the transcriptional activators GCN4 from yeast and zeste from drosophila (Chen, J. D., supra; Thireos, G., supra). Taken together, these observations suggest that the wcs120 promoter possesses putative cis-acting elements that could bind known transcription factors, present in both the plant and animal kingdoms.

The promoter region of the wcs120 gene was also analyzed by 3' deletions. The deletion of the proximal 67 bp of the wcs120 promoter leads to a decrease of the FI from 8.0 to 4.0-fold, suggesting the presence of a LTRE in the region between −67 and +1. A further deletion to −178 decreases the FI from 4.0 to 1.8-fold, suggesting the presence of a LTRE. This supports the observation made from the analysis of the −215 to −72 deletion. Upon removal of the initial 268 bp of the promoter, the activity at 4° C. increased whereas that at 24° C. decreased compared to −178 construct. The relative increase of the FI suggests the existence of negative regulatory elements between −268 and −178 that would be mainly active at 4° C. Deletion to −374 completely abolishes the wcs120 promoter activity. Since the most important loss of absolute activity is that at 4° C., an LTRE may be present between −374 and −268. On the other hand, we cannot rule out the possibility of the existence of an enhancer element in this region. Further deletion to −501 does not reactivate the promoter, indicating that most of the elements responsible for the promoter activity were removed.

Together, the results from the transient expression assays show that transcription of the wcs120 gene is dependent on the presence of regulatory elements in the promoter region alone or in combination.

In an embodiment of this invention the full length promoter and any derivative thereof, of the wheat wcs120 gene have the capability of inducing an 8 fold increase in gene expression at LT over and above the expression at room temperature. Different deletion fragments of the promoter and any derivative thereof of the instant invention, are capable of inducing gene expression in response to a change in temperature, particularly at low temperature. Thus, there is provided the means to use the wheat wcs120 gene promoter and any variants, derivatives and/or fragments thereof to drive a gene expression in response to LT. Particularly, the promoter fragment −414 to +1 is the most performing in increasing gene expression. It is contemplated that a promoter wherein transcription repressor binding regions have been deleted (from about −590 to −415, without being restricted to these exact positions), could be even more performing.

In another embodiment of this invention the promoter, and any variant, derivative and/or fragment thereof can be operatively linked to any gene of interest, transformed into a plant for the purpose of inducing expression of the gene of interest in response to low temperature. The product of the gene expressed under low temperature, can then be recovered.

4.2 Activity of the WCS120 Promoter in Different Species

Figure 10:
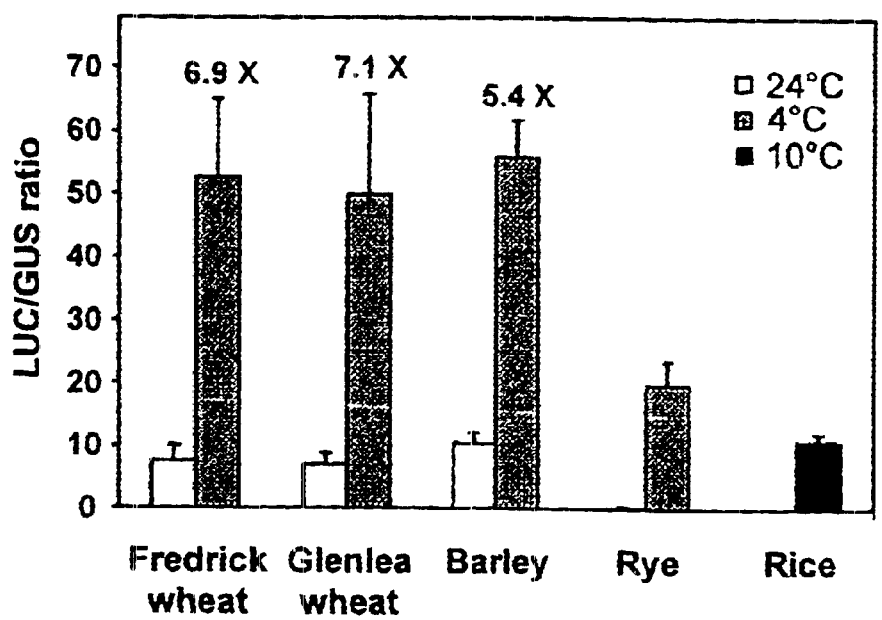
FIG. 10 Activity of the wcs120 full length promoter in different monocotyledonous species after cold exposure. The leaf sections were transformed with the FL860LUC construct and Ubi-gus (pAHC27), and incubated at LT for 3 days or at 24° C. for 2 days. The LT treatment was performed at 4° C. except for rice, a sensitive species, which was exposed al 10° C. Soluble proteins were extracted and enzymatic activities of LUC and GUS were determined. Numbers above the error bars indicate the fold induction (FI; 4° C./24° C. relative activity ratio). In the case of rye and rice, the FI was difficult to estimate due to the undetectable activity of LUC at 24° C. The LUC/GUS ratio was almost zero.

The transient activity of the full length promoter (FL860) was determined in different freezing sensitive and tolerant species. The results show that the promoter activity is similar in the more tolerant Fredrick and less tolerant Glenlea cultivars (FIG. 10). This suggests that even though Glenlea is less tolerant, the plant possesses the trans regulatory elements needed to express this important gene for FT. This result was expected since northern analysis had shown no significant differences between the levels of expression of the wcs120 gene in Glenlea and Fredrick, during the first week of acclimation (Hughes, M. A., et al. (1996) J. Exp. Bot. 47: 291–305). The kinetic analyses of WCS120 protein accumulation and the close inverse relationship between WCS120 protein levels and $LT_{50}$ indicate that the FT of cereals is determined by the degree and duration of LT gene expression. These results and other evidence, such as increased transcript stability and alternative splicing, support a role for post-transcriptional regulation events in the differential accumulation of proteins at LT (Hughes, M. A., supra; Bournay, A. S., et al. (1996) Nucleic Acids Res. 24: 2347–2351).

The promoter shows a similar LT-inducibility in wheat and barley (FIG. 10). Barley, a species closely related to wheat, possesses a gene dhn5; (Close, T. J., supra) that is almost identical to wcs120. Winter rye, a highly tolerant Gramineae that also possesses homologs of the wcs120 family members, showed a 20-fold increase in activity following exposure to 4° C. Rice, a cold-sensitive monocot species that possesses an inactive gene homologous to wcs120, showed an 11-fold increase at 10° C. compared to 24° C. A much higher LT-inducibility was observed in the freezing tolerant dicot species alfalfa and Brassica at 4° C. (Table 2). The fold increase was very difficult to estimate due to the undetectable activity of wcs120-LUC at 24° C. The wcs120 promoter activity was also evaluated in cold-sensitive dicots. The results shown in Table 2, demonstrate the activity of the wcs120 full length promoter in different dicotyledonous species after cold exposure. The leaf sections were transformed with the FL860LUC construct and Ubi-gus (pAHC27), and incubated at LT for 3 days or at 24° C. for 2 days. The LT treatment was performed at 4° C. or at 10° C. for the cold tolerant and sensitive species, respectively. Though these experiments were conducted at 4° C. and at 10° C., the promoter, derivatives, variants or fragments thereof are capable of inducing expression of a gene with a temperature of about 15° C. and less. Soluble proteins were extracted and enzymatic activities of LUC and GUS were determined. In cucumber, a 26-fold induction of the activity at 10° C. was observed. On the other hand, in tomato, no difference in activity was observed between the samples treated at the two temperatures. Pepper is the only species for which a decrease (10-fold) of the promoter activity was observed upon LT exposure. These results indicate that the level of promoter activity is not correlated with the capacity of these species to develop FT. For example, the promoter is less active in rye (the most tolerant species tested) than in wheat, a result that is supported by previous genetic analyses. Amphiploids from rye/wheat crosses show a FT equivalent, but not superior, to that of wheat (Hughes, M. A., supra). Furthermore, the level of expression of the wcs120 family genes in these individuals does not exceed that observed in wheat. This suggests that the elements important for FT in rye are silenced in a predominant wheat background, and would suggest the existence of differences in the cis and/or trans-acting elements involved in the transcription of wcs120 and perhaps of other LT-induced genes.

latter family is not known. The results provide evidence of the existence of common transcription factors in both monocots and dicots, and suggest that these factors have the capacity to recognize the cis-acting elements of a cold-inducible heterologous promoter. The data presented here indicate that the cold sensitivity of some species (such as rice and cucumber) is apparently not due to inefficient or absent transcription factors but may possibly result from the inefficiency of the promoters of the homologous genes.

The identification of this promoter is of importance from an application point of view since it could be a useful tool in the elaboration of strategies aimed at the improvement of FT in sensitive monocot and dicots species. Until now, plants modified to overexpress genes potentially implicated in FT have been transformed with constructions bearing the genes under the control of constitutive promoters. The most widely used promoters are those of the maize ubiquitin gene (Ubi) and of the CaMV 35S gene, for monocots and dicots respectively. Efforts are now being focused towards the identification of promoters that are more efficient in different plants. For example, several constructions bearing, in different combinations, fragments of the CaMV 35S promoter, an intron of the bean phaseolin gene, the $\Omega$ sequence of TMV and terminating sequences from the CaMV 35S or nos genes have been tested in rice (monocot) and tobacco (dicots) (Mitsuhara, I., et al. (1996) Plant Cell Physiol. 37: 49–59). It was shown that the most efficient constructions for rice were not the same as for tobacco, suggesting differences in the specificity of gene expression between monocot and dicots plants. On the other hand, the overexpression of a gene resulting from the use of a constitutive promoter is not necessarily an objective to achieve in all cases. Indeed, few studies have focused on the physiological consequences related to the constitutive expression of genes that are normally inducible and thus expressed only when needed. The use of a cold-inducible promoter such as that of the wcs120 gene would allow the expression of the genes only when the plant is under cold stress conditions.

There is provided a promoter sequence, fragments, derivatives or variants capable of inducing gene expression under adverse environmental conditions. More specifically the promoter sequence of this invention would induce gene expression under temperature stress conditions, more specifically, under cold stress conditions.

CONCLUSION

It will be appreciated that the methods and compositions of the present invention can be incorporated in the form of

TABLE 2

| Species | Family | Tolerance to freezing | LUC/GUS ratio | | |
| --- | --- | --- | --- | --- | --- |
| | | | 24° C. | cold | FI[a] |
| alfalfa | Leguminosa | tolerant | 0[b] | 1031 ± 109 | (ND)[b] |
| Brassica | Cruciferae | tolerant | 0[b] | 39 ± 2 | (ND)[b] |
| cucumber | Cucurbitaceae | sensitive | 197 ± 44 | 5117 ± 743 | 26 |
| tomato | Solanaceae | sensitive | 73 ± 21 | 59 ± 29 | 1[c] |
| pepper | Solanaceae | sensitive | 18702 ± 11557 | 1957 ± 405 | 0.1 |

[a]The fold induction (FI) is the cold/24° C. relative activity ratio.
[b]The FI was difficult to determine due to the undetectable activity of LUC at 24° C.
[c]The difference between the two conditions is not significant Our data indicate that the wcs120 promoter is LT-inducible in the Gramineae (wheat, barley, rice and rye), Cruciferae (Brassica), Leguminosae (alfalfa) and Cucurbitaceae (cucumber), but not in the Solanaceae family (tomato, pepper). The reason of the absence of LT induction in the a variety of embodiments, only a few of which are disclosed herein. It will be apparent to a person skilled in the art that other embodiments exist that do not depart from the spirit of the invention. Thus, the described embodiments are illustrative and should not be construed as restrictive.

What is claimed is:

1. An isolated DNA sequence including a cold inducible promoter, wherein the promoter comprises the nucleotide sequence of SEQ ID NO: 1, bases 645 to 860 of SEQ ID NO: 1, or bases 1 to 592 of SEQ ID NO: 1.

2. The DNA sequence of claim 1, wherein the promoter is operatively linked to a gene.

3. The DNA sequence of claim 2, wherein the gene encodes a protein involved in conferring low temperature tolerance or freezing tolerance to a plant.

4. A vector comprising the DNA sequence of claim 2 or 3, wherein the vector is capable of being transformed into a host selected from the group consisting of a plant, plant tissue, and plant cell.

5. The vector of claim 4, wherein the host is monocotyledonous or dicotyledonous.

6. The vector of claim 4, wherein the promoter induces or regulates transcription at a temperature equal to or less than about 15°.

7. The vector of claim 4, wherein the promoter induces or regulates transcription at a temperature equal to or less than about 4°.

8. The DNA sequence of any one of claims 1–3, wherein the promoter comprises SEQ ID NO: 1.

9. The DNA sequence of any one of claims 1–3, wherein the promoter comprises bases 1 to 860 of SEQ ID NO: 1.

10. The DNA sequence of any one of claims 1–3, wherein the promoter comprises bases 270 to 860 of SEQ ID NO: 1.

11. The DNA sequence of any one of claims 1–3, wherein the promoter comprises bases 445 to 860 of SEQ ID NO: 1.

12. The DNA sequence of any one of claims 1–3, wherein the promoter comprises bases 645 to 860 of SEQ ID NO: 1.

13. A recombinant plant including the DNA sequence of any one of claims 1–3.

14. A method of increasing transcription of a gene at low temperature in a plant, which comprises:

(a) growing a recombinant plant including the DNA sequence of claim 2 and (b) lowering the temperature to about 15° C. or less to induce transcription of said gene.

15. A method for producing a protein in a plant, which comprises:

(a) growing a recombinant plant including the DNA sequence of claim 2, wherein said gene encodes a protein of interest;

(b) expressing the protein encoded by said gene; and (c) isolating the protein.

16. A method of increasing a plant's tolerance to low temperature or freezing, which comprises:

(a) growing a recombinant plant including the DNA sequence of claim 3 and (b) lowering the temperature to about 15° C. or less, thereby inducing expression of said protein and conferring low temperature or freezing tolerance to the plant.

17. The method of any one of claims 14–16, wherein the plant is monocotyledonous or dicotyledonous.

18. The method of any one of claims 14–16, wherein the plant is selected from the group consisting of Gramineae, Cruciferae, Leguminosae and Cucurbitaceae.

19. The method of any one of claims 14–16, wherein the plant is selected from the group consisting of wheat, barley, rice, rye, Brassica, alfalfa and cucumber.

20. The DNA sequence of any one of claims 1–3, wherein the promoter comprises bases 1 to 592 of SEQ ID NO: 1.

21. The DNA sequence of any one of claims 1–3, wherein the promoter comprises bases 1 to 682 of SEQ ID NO: 1.

22. The DNA sequence of any one of claims 1–3, wherein the promoter comprises bases 1 to 793 of SEQ ID NO: 1.

* * * * *